United States Patent [19]

Morré

[11] Patent Number: 5,643,853
[45] Date of Patent: Jul. 1, 1997

[54] THIOL ACTIVATION OF CYTOTOXIC AND AUXIN-HERBICIDAL AGENTS AND ROOT FORMATION STIMULATION

[75] Inventor: D. James Morré, West Lafayette, Ind.

[73] Assignee: Purdue Research Foundation, West Lafayette, Ind.

[21] Appl. No.: 397,659

[22] Filed: Feb. 28, 1995

[51] Int. Cl.$^6$ .......................... A01N 43/40; A01N 39/02; A01N 39/04; A01N 37/10

[52] U.S. Cl. .......................... 504/130; 504/144; 504/145; 504/254; 504/323; 504/324; 47/58; 47/DIG. 3; 435/7.4; 435/25; 514/592; 514/706

[58] Field of Search .................................. 504/130, 144, 504/145, 254, 323, 324

[56] References Cited

U.S. PATENT DOCUMENTS 4,169,720  10/1979  Schacht et al. ............................ 71/108
4,396,418  8/1983  Schirmer et al. ............................ 71/98

OTHER PUBLICATIONS

Morré et al. "Selective Inhibition of Auxin–Stimulated NADH Oxidase Activity and Elongation Growth of Soybean Hypocotyls by Thiol Reagents", *Plant Physiology*. 107:1285–1291. Apr. 1995.

Morré et al. "Auxin–Modulated Protein Disulfide–Thiol–Interchange Activity from Soybean Plasma Membranes", *Plant Physiology*. 109:573–578. Oct. 1995.

Standardi, et al., Effects of Some Antioxidants on in Vitro Rooting of Apple Shoots (1990) HortScience 25(11):1435–1436.

Centre horicole de Lullier, Ecole d'ingenieurs ETX, 1254 Lullier, Switzerland, II.1 Rooting of in Vitro Cuttings (1991) Biotechnology in Agriculture and Forestry, vol. 17, 231–261.

Lane, Regeneration of Apple Plants from Shoot Meristem–Tips (1978) Plant Science Letters, 13 281–285.

*Primary Examiner*—S. Mark Clardy
*Attorney, Agent, or Firm*—Flehr Hohbach Test Albritton & Herbert LLP

[57] ABSTRACT

Thiol compounds are employed in conjunction with compounds which modulate self proliferation, both as to plants and mammals. The thiol compounds find effect in enhancing the effectiveness of auxin like compounds, either as herbicides or in enhancing root formation. In addition, thiol compounds act in conjunction with cytotoxic agents in mammals to allow for lower dosages of the cytotoxic agents while retaining the cytotoxic effect against hyperproliferative diseases, such as cancer. The combination finds particular effect against cells dependent upon an isoform of a surface membrane NADH oxidase for proliferation.

9 Claims, No Drawings

THIOL ACTIVATION OF CYTOTOXIC AND AUXIN-HERBICIDAL AGENTS AND ROOT FORMATION STIMULATION

INTRODUCTION

TECHNICAL FIELD

The field of this invention is the killing of proliferating cells and enhancing root formation.

BACKGROUND

There are many situations where one wishes to modulate cellular growth. Since all of life is dependent upon cellular regeneration, there is substantial interest in being able to modulate cellular growth in the plant and animal kingdoms. In the case of plants, one wishes to encourage the growth of desirable plants, such as plant crops and flowers, while at the same time one wishes to discourage the growth of weeds, both pre-germination and post-germination of the desired plant. In many situations one wishes to kill all vegetation, such as highway borders, pathways, graveled areas, and the like. However, many of the herbicides which are used today pollute the environment in introducing undesirable elements into the soil, which can then be leached into aquifers, streams and rivers. There is, therefore, substantial interest in being able to reduce the amount of herbicidal use without further pollution of the environment.

There is also the need to root stock to expand desired plants, particularly woody stock. Better methods are needed to increase the efficiency and reduce the time for rooting.

Finally, there is the proliferation of cells in the animal kingdom. The development of the various species from a single fertilized cell to the mature adult requires rapid proliferation. However, during the life of the organism, there are many situations where rapid proliferation is undesirable. Various diseases associated with rapid proliferation include cancers, psoriasis, restenosis, and the like. Many of the agents used for treating these diseases, are cytotoxic agents which attack all proliferating cells and frequently have substantial side effects in addition to their cytotoxic activity.

Various techniques have been employed to reduce the systemic influences of these cytotoxic drugs. Immunotoxins employ a toxin joined to an antibody, where the antibody is specific to varying degrees for a marker present on cancer cells. Another technique which is limited to physical access to the tumor employs the cytotoxic drug in a matrix which reduces the translocation of the cytotoxic drug from the site of the lesion. Other techniques have involved use of liposomes with agents, such as antibodies, to direct the liposomes to the target, where the lumen of the liposome comprises a cytotoxic agent. However, none of these techniques has found universal acceptance. So long as one continues to use the cytotoxic drugs in systemic fashion, there is substantial interest in finding ways to diminish the amount required for an effective dosage as a cytotoxic agent.

RELEVANT LITERATURE

The classic method of root induction is to utilize an auxin shock. Lane (1978) Plant Sci. Lett. 13:281–285 and Moncousin (1992) Rooting of in vitro Cuttings. In: Biotechnology in Agriculture and Forestry (YPS Bajag, ed.) Springer Verlag, Heidelberg, 17:231–261. Standardi and Romani (1990) Hort. Sci. 25:1435–1436 teaches auxin shock for rooting and employs cysteine.

SUMMARY OF THE INVENTION

Thiol compounds are employed as adjunctive agents to enhance modulation of cellular proliferation. Particularly, the thiol agents are found to enhance cytotoxicity, both in plants and animals, as well as enhancing root formation in conjunction with auxins or auxin shock.

DESCRIPTION OF THE SPECIFIC EMBODIMENTS

Methods and compositions are provided for modulation of cellular proliferation in plants and animals. Particularly, the thiol compounds are used in conjunction with cytotoxic agents to reduce the amount of the cytotoxic agent required for cytotoxicity. By combining the thiol compound with the cytotoxic agent, either locally or systemically, substantially smaller amounts of cytotoxic agent are required in order to achieve desired levels of cytotoxicity. In mammals, one may use combinations of cytotoxic agents plus thiol compound to control the growth of cells in proliferative diseases, such as cancer. The combination may be administered systemically or locally.

CYTOTOXICITY OF PLANT CELLS

The control of undesired vegetation will be considered first. The subject compositions comprise an auxin-type herbicide, e.g. 2,4-dichlorophenoxyacetic acid and triclopyr, optionally in conjunction with ammonium nitrate, and the thiol compound. The auxin type herbicide may be used as an acid derivative, particularly salts and esters, where the ester group may be of from 1 to 12 carbon atoms and the salts may include amino salts of from 0 to 12 carbon atoms. These derivatives are well known in the literature and commercially available.

A wide variety of thiol compounds may be employed, the primary consideration will be economics, convenience, effect on the environment, ease of formulation, handling characteristics, physiological activity toward mammals, and the like. A number of thiol compounds are available and may be used, such as cysteine, glutathione, dithiothreitol, thiolpropionic acid, etc. For the most part, the compounds will generally be from about 2 to 12, usually 2 to 10 carbon atoms, and may have other functionalities, such as oxy, oxo, including esters and amides, amino, etc. As indicated above, the choice of mercaptan is not critical to this invention, so long as it is not too volatile, does not have an offensive odor, and can be readily handled.

Depending upon the particular auxin-type herbicide employed, one will normally use less than about 60%, usually less than about 50%, and generally more than about 20% of the dosage necessary for herbicidal activity of the auxin-type herbicide, by itself, or in conjunction with ammonium nitrate. The amount employed will vary depending upon the particular vegetation involved, the degree to which one wishes to kill the vegetation and the rapidity with which the vegetation is to be killed. Thus, where it is sufficient that only a portion of the wild vegetation be killed, milder formulations may be employed, where rapid complete death is desired, the formulations will be stronger.

Generally, the amount of herbicide will vary with the particular herbicide, generally ranging from about 1 to 6 pounds per acre, preferably from about 1 to 5 pounds per acre, more preferably from about 2 to 4 pounds per acre. When ammonium nitrate is present, it will generally range from about 0.025 to 2 pounds per acre, more usually from about 0.05 to 1.5 pound per acre. The thiol compound will vary to some degree based on the particular thiol compound but will generally be in the range of about 0.01 to 2 pounds per acre, more usually in the range of about 0.025 to 1.5 pounds per acre, and preferably 0.05 to 1 pound per acre.

Formulations of particular interest for total vegetative kill include 3 to 5 pounds per acre of the herbicide, particularly triclopyr, 1 to 2 pounds per acre of ammonium nitrate, and 0.05 to 0.25 pounds per acre of cysteine.

The subject formulations can be formulated in a variety of ways, such as dispersible dry powders, pellets, solutions, or the like. In the formulation, the weight ratio of thiol compound to herbicide will be generally in the range of about 1:2–100, more usually in the range of about 1:10–100, while the ratio of the ammonium nitrate to herbicide will generally be in the range of about 1:1.5–100 more usually 1:2–50.

Other additives and excipients may be included in the formulation, depending upon the manner in which the formulation will be applied. Other additives which may be included in minor amounts include spreading agents, penetrating agents, surfactants, emulsifiers, etc., with the other components in appropriate relationship.

The subject compositions can be used pre-emergent, and may find application post-emergent, particularly as a spray, although pellets may also be used and scattered. For the spray, the herbicide will generally be about 1 to 10, more usually 2 to 8, preferably 3 to 6 pounds per 100 gallons, the ammonium nitrate if present, will generally be 0.5–5, usually about 2 to 4, pounds for 100 gallons and the thiol compound will generally be about 0.1 to 1, more usually about 0.1 to 0.5 pounds for 100 gallons. The composition may be provided as a concentrate, for further dilution, where the herbicide will be from about 1 to 5 pounds per gallon, usually employing an emulsifier.

In some instances, combinations of herbicides may be employed, such as combinations of triclopyr, picloram, 2,4-D, glyphosate, clopyralid, fanoxaprop-ethyl, oxadiazon, bromoxynil, propanil, dicamba, and the like, where the additional herbicide may provide specific advantages for particular applications. Generally, the weight ratio of the secondary herbicide(s) to the primary auxin type herbicide described above, will generally be from about 0.01–0.5:1, more usually from about 0.05–0.25:1.

When spraying, the application rate will generally provide the amount of herbicidal composition indicated above. Conveniently, one may provide for formulations which allow for spraying at about 10 to 50 gallons per acre, more usually at about 15 to 35 gallons per acre.

The subject formulations are particularly applicable to woody trees and brush, where the species are resistant to the auxin-type herbicide, by itself or in conjunction with other herbicides. The subject compositions are found to be effective for non-evergreen roadside vegetation and deciduous wood species, such as ash and hard maple.

Species that are controllable and very sensitive to the herbicides include briars (blackberry, raspberry, etc.), mulberry, walnut, sumac, sassafras, box elder, buckeye, cottonwood, wild grape and poison ivy; species that are sensitive include red bud, elm, honey locust, black locust, hackberry, willow, and white oak; species of intermediate sensitivity include hard maple and black cherry; and species that are resistant include juniper and ash, all of which can be controlled by the subject formulation.

CYTOTOXICITY OF MAMMALIAN CELLS

The thiol compounds act via alterations in the activity patterns of a growth-related NADH oxidase (disulfide-thiol interchange protein). This activity is altered in cancer and a protein earing this altered activity circulates in the blood. The circulating form of the cancer associated altered form of the NADH oxidase has been designated as t-NOX and is useful as a diagnostic procedure for cancer. The thiol compounds find use as an enhancer of in conjunction with diagnostic uses of drugs acting as inhibitors of t-NOX. With patient sera treated with 1 μM to 100 μM capsaicin, the maximum inhibition of NADH oxidation with serum is 15 to 40%. However, if the capsaicin treatment is followed by 0.1 to 10 μM reduced glutathione, a pronounced additional transient inhibition of 5 to 10 min duration is observed. This inhibition is not observed with sera of normal patients.

The thiol compounds can also find use for reactivation of sample preparations that have been frozen prior to use in a diagnostic assay for cancer associated t-NOX. Addition of 0.1 to 10 μM of oxidized glutathione to such preparations restores the enzymatic activity. Inclusion of up to an equivalent amount of reduced glutathione with the serum samples during storage will also help maintain enzyme activity. Comparable amounts of oxidized thiol compounds other than oxidized glutathione also find use.

For use in mammals to inhibit cellular hyperproliferation particularly in association with cancer, various cytotoxic agents may be used in conjunction with thiol compounds. The subject compositions may be used with any type of cancer, whether solid or dispersed, including carcinomas, sarcomas, lymphomas, melanomas, and the like. The cancers may be associated with various tissues and organs, such as blood, breast, prostate, ovary, lung, kidney, liver, eye, skin, pancreas, bone, bone marrow, leukocytes, etc.

Chemotherapeutic drugs which may be employed include enzyme inhibitors, proliferation inhibitors, lytic agents, DNA synthesis inhibitors, membrane permeability modifiers, DNA intercalators, antimetabolites, or the like. Illustrative drugs include chlorambucil, melphalan, busulfan, carmustine, lomustine, streptozotocin, thiotepa, dacarbazine, methotrexate, 5-flurouracil, cytarabine, azaribine, mercaptopurine, thioguanine, vinblastine, vincrinistine, actinomycin D, adriamycin, bleomycin, mithramycin, mitomycin C, L-asparaginase, cisplatin, sulfonylureas, capsaicin, and its derivatives, and the like. Of particular interest are drugs which inhibit a surface membrane NADH oxidase associated with the hyperproliferative state. These compounds include adriamycin, sulfonylureas, capsaicin, and the like.

The chemotherapeutic drug will normally be used in an amount of from about 10 to 80 weight percent, more usually from about 10 to 60 weight percent, particularly from about 20 to 60 weight percent of the normal chemotherapeutic dosage. The thiol compounds, depending upon the particular drug, may be formulated together with the chemotherapeutic drug or separately and combined immediately prior to administration or concomitantly or consecutively with administration of the chemotherapeutic drug. The amount of the thiol compound which finds use in proportion to the amount of chemotherapeutic drug will generally be optimized within the ratio of about 0.01 to 10, more usually from about 0.05 to 1 of thiol compound to chemotherapeutic drug. Thiol compounds of interest include cysteine, glutathione, thiolacetic acid, cysteine, 2-mercaptoethanol, dithiothreitol, mercaptamine, etc.. Since the thiol compounds will normally be physiologically acceptable and relatively large amounts of the thiol compound can be used without adverse physiological effect, once the minimum amount is defined for the desired therapeutic activity, one may use increasingly larger doses of the thiol compound without adverse effect and frequently without any further advantage.

The subject composition may be used both in vitro and in vivo. In many situations, it is desirable to inhibit growth of cancer cells in the presence of normal cells in culture. By augmenting the activity of the chemotherapeutic agent, with an agent such as the thiol compound which does not normally have adverse physiological effects, one can substantially reduce the adverse effect of the chemotherapeutic agent on the normal cells. In this manner, one can minimize the adverse effects on normal cells, while insuring the substantial absence or absence of tumorous cell growth. The chemotherapeutic agent and thiol additive may be maintained at a substantially constant concentration replenishing the culture medium on a regular basis, conveniently by substituting one half of the culture medium on a schedule of from 1 to 7 days.

For use in mammals, the subject compositions can be introduced intralesionally or parenterally, particularly intravascularly or intramuscularly. For intralesional administration, the subject compositions may be injected directly into the lesion, by themselves or in conjunction with vasoconstrictive agents, and/or matrices, such as collagen, fibrinogen, heparin, or the like, individually or in combination. See, particularly, U.S. Pat. No. 4,619,913. Generally, the amount of drug will range from about 0.01 to 30% of the composition depending upon the nature of the drug. Usually, the amount of cytotoxic drug administered to the tumor site will range from about 0.01 to 500, more usually about 0.05 to 300 mg/kg of the host. As illustrative, about 50 to 200 µM of a chemotherapeutic sulfonylurea localized concentration is provided. The thiol concentration will therefore be in the range previously indicated in relation to the chemotherapeutic agent.

For intravascular administration, the formulation may be present in any convenient physiologically acceptable medium, to provide a systemic concentration of the chemotherapeutic agent in proportion to the normal dosage. Carriers may include water, saline, phosphate buffered saline, vegetable oils, ethanol, or the like. Concentrations may be varied widely, depending on the manner of administration, solubility of the chemotherapeutic agent, etc. Small amounts of other additives may be present, such as emulsifiers, stabilizers, buffers, and the like. In some instances, the subject formulation may be provided in the lumen of a liposome for slow or directed release.

ROOTING OF SHOOTS

Rooting is carried out in three phases. Phase 1 is induction (0 to 3 or 4 days.) Phase 2 is dedifferentiation and the formation of root meristems (1 to several weeks). phase 3 is growth and emergence of new roots (several weeks to 1 month). In some situations, especially with plantlests in vitro, the induction phase following the auxin shock is carried out in darkness (up to 5 days). Thereafter, rooting is either in continuous light or alternating light and dark cycles appropriate to the species. For stem cuttings, all 3 phases of rooting are carried out either in continuous light or under alternating dark and light cycles appropriate to the plant material.

In conjunction with rooting, thiols may be used as adjuvants to enhance root stimulation, particularly with difficult-to-root varieties. The thiol compounds described above, particularly cysteine and dithiothreitol, find use in this application in conjunction with auxins in the growth medium or auxin shock. Auxins include indole-3-acetic acid, indole-3-butyric acid, α-naphthaleneacetic acid, etc. Prior to auxin shock, the cuttings or shoots may be subject to maintenance in the dark from 0.5 to 2 weeks under mild conditions. The auxin shock may be carried out as appropriate, generally employing from about 0.5 to 5 mM of an appropriate auxin, conveniently 1–2 mMindole-3-acetic acid (IAA). The auxin shock is performed in a conventional manner, conveniently using an agarized solution and placing the microcutting into the solution for from 0.5 to 5, more usually from about 0.5 to 3, and preferably from 1 to 2 h. The timing may vary depending upon the particular species and its resistance to formation of roots. The microcuttings may be obtained from callus, tissue, intact plants or other appropriate plant parts or sources of growing tissues where formation of roots might be desirable. The auxin solution will be in a solvent comprising such other additives as minerals, vitamins, salts, buffers, detergents, stickers, wetting agents, spreaders and other growth enhancers.

Instead of auxin shock, a combination of auxin and thiol compound can be employed in the rooting medium. Various conventional rooting mediums may be employed such as Murashige and Skoog mineral solutions with conventional additives, such as inositol, thiamine, nicotinic acid, indolebutyric acid and a carbon source e.g. sucrose; a woody plant medium mineral solution (Lloyd and McCown,(1981) Int. Plant Prop. Soc. Proc. 30:421–427) supplemented with vitamins (Mullin et al. (1974) Phytopath. 64:1425–1429) and amino acids (Skoog (1944) Am. J. Bot. 31:19–24), with plant growth regulators, such as benzylaminopurine and alpha-naphthylacetic acids, with a carbon source and an amino acid source, such as Difco bactoagar. The amount of auxin in the rooting medium will be about 2 mM. The particular medium will be selected in accordance with conventional ways for the particular plant.

The thiol compound may be provided with the auxin shock or auxin continuously or intermittently during the first 10 days of maintenance in the shooting medium. After the auxin shock, the cuttings or shoots are rinsed and then introduced into an agar medium or distilled water comprising the appropriate composition. The thiol compound will generally be present in about 0.05 to 5 mM, preferably about 0.1 to 2 mM, where the response may vary with the particular thiol source and the time at which the thiol compound is provided. Usually, during growth, the thiol compound will be provided over at least one day and may be provided during the entire period, with some preference for the first one to three day on the six to nine day periods from the initiation or rooting stimulation with the auxin shock or auxin containing rooting medium. A wide variety of monocots and dicots both non-woody and woody plants, may be used with the subject formulation. Illustrative plants include apple, dipladenia, daphne, mung bean, soybean, Hedera, Forsythia, Salix, various Prunus species, Chrysanthemum, Poinsettia, Acacias, Acer, Alnus, Azalea, Bougainvillaea, Bouvardia, Castanea, Carica, Chaelomenes, Cercis, Citrus, Cornus, Corylus, Cotinus, Eucalyptus, Cydonia, Fagus, Gardenia, Garrya, Ginko b., Hamamelis, Hydrangea, Ilex, Kalmia, Malus, Pieris, Pyrus, Quercus, Ribes, Rosa, Skimmia, Syringa, Vaccinium, Viburnum, Vitis, Rubus, Spirae and various other fruit-bearing, ornamental and commercially-utilitarian woody species as well as flowers, vegetables and agricultural and horticultural crop species as well as conifers and evergreens.

The following examples are offered by way of illustration and not by way of limitation.

EXPERIMENTAL

I. Effect of Thiol Compounds on Activity of Herbicides

A number of studies were performed to evaluate the effect of various combinations of auxin like compounds, with and without ammonium nitrate, and without a thiol additive and with different thiol additives on a variety of weeds and woody shrubs. These particular plant species are frequently found in areas where vegetation is undesired and there is a strong interest in maintaining the area substantially free of vegetation. The results of the studies are set forth in a series of tables, tables 1 to 9.

TABLE 1

Comparison of triclopyr (Garlon-4) and the ammonium nitrate additive combined with TR-III (Cysteine) on control of ash and hard maple. IN-126 test area. Treatments were applied August 10, 1993. Evaluations were on October 14, 1993.

| Triclopyr | Ammonium nitrate | Amount/40 gal water X-77 surfactant | TR-III | Defoliation, % Ash | Hard Maple |
|---|---|---|---|---|---|
| 2 lb | 1 lb | 0.1 gal* | None | 60 ± 10 | 50 ± 10 |
| 2 lb | 1 lb | 0.1 gal | 1 lb | 90 ± 10 | 100 ± 0 |

*0.25% of the total spray mixture

TABLE 2

Effect of cysteine in combination with 2,4-D and triclopyr on kill of white clover (*Trifolium repens*).

| | | % Dead | | | |
|---|---|---|---|---|---|
| Herbicide | Cysteine 0.05 lb/A | Applied 5/31/94, Evaluated 6/6/94 | Applied 6/1/94, Evaluated 6/22/94 | Applied 6/6/94, Evaluated 6/19/94 | Applied 6/7/94, Evaluated 7/5/94 |
| None | − | 0 | 0 | 0 | 0 |
|  | + | 0 | 0 | 0 | 0 |
| 2,4-D, | − | 30 | 20 | 15 | 20 |
| 5 lb/A | + | 50 | 40 | 30*** | 30*** |
| Triclopyr, | − | 60 | 60 | 50 | 60 |
| 5 lb/A | + | 80* | 80*** | 70*** | 100*** |

*90% kill on 6/12/94 and 100% kill on 6/19/94.
**90% kill on 6/27/94.
***Contained 1 lb/A ammonium nitrate.

TABLE 3

Comparison of cysteine and glutathione in combination with 2,4-D and triclopyr on kill of white clover (*Trifolium repens*).

| | | | | % Dead | |
|---|---|---|---|---|---|
| Herbicide | Cysteine | Glutathione | Dithiothreitol | Applied 6/8/94, Evaluated 7/5/94 | Applied 6/9/94, Evaluated 6/19/94 |
| 2,4-D, 2 lb/A | — | — | — | 20 | 20 |
|  | 1 lb/A | — | — | 30 | 30 |
|  | — | 1 lb/A | — | 50 | — |
|  | — | — | 1 lb/A | — | 30 |
| Triclopyr, 2 lb/A | — | — | — | 90 | 40 |
|  | 1 lb/A | — | — | 100 | 50 |
|  | — | 1 lb/A | — | 90 | — |
|  | — | — | 1 lb/A | — | 60 |

TABLE 4

Dose response of reduced glutathione, dithiothreitol and cysteine on herbicidal activity of 3.5 lb/A triclopyr on white clover (Trifolium repens). Applied 6/30, 7/1/94* and 7/6/94**. Evaluated 7/20/94, and 7/23/94****.

| | % Dead | | |
|---|---|---|---|
| Rate/A | Glutathione** | Dithiothreitol*** | Cysteine**** |
| 0 | 5 | 20 | 50 |
| 0.05 | 90 | 40 | 60 |
| 0.1 | 100 | 50 | 50 |
| 0.1* | 100 | 50 | 30 |
| 0.5 | 80 | 40 | 60 |
| 1 | 80 | 50 | 40 |

*+0.1 lb/A ammonium nitrate

TABLE 5

Enhancement of herbicidal activity of 5 lb/A triclopyr on white clover (Trifolium repens) by ammonium nitrate. Applied 6/16/94. Evaluated 6/26/94.

| Ammonium nitrate, lb/A | % Dead |
|---|---|
| 0 | 40 |
| 0.05 | 55 |

TABLE 6

Dose response of cysteine in the presence of 2 lb/A triclopyr and 1 lb/A ammonium nitrate on white clover (Trifolium repens).

| | % Dead | | |
|---|---|---|---|
| Cysteine Rate/A | Applied 7/6/94 Evaluated 7/23/94 | Applied 7/7/94 Evaluated 8/1/94 | Average |
| 0 | 80 | 50 | 70 | 67 |
| 0.025 | 100 | 80 | 90 | 90 |
| 0.05 | 80 | 60 | 90 | 77 |
| 0.1 | 90 | 60 | 80 | 77 |
| 0.5 | 100 | 60 | 80 | 80 |
| 1 | 100 | 80 | 80 | 87 |

TABLE 7

Control of common milkweed (Asclepias syriaca) and canada thistle (Cirsicum arvense) by triclopyr + ammonium nitrate + cysteine.

| Rate/A, lb | | | % Dead | | |
|---|---|---|---|---|---|
| Triclopyr | Ammonium Nitrate | Cysteine | Milkweed (Asclepias syriaca) | Canada thistle (Cirsicum arvense) | Field Bindweed (Concolculus arvensis) |
| 2 | — | — | 20 | 30 | 92 |
| 2 | 1 | 0.1 | 30 | 40 | 96 |
| 2 | 1 | 1 | 50 | 50 | 95 |
| 5 | — | — | 80 | 70 | 95 |
| 5 | 0.05 | 0.05 | 100 | 50 | 98 |

1 Applied 7/11/94. Evaluated 8/20/94.
2 Applied 7/12/94. Evaluated 7/25/94.
3 Applied 7/13/94. Evaluated 8/3/94.

TABLE 8

Response to two rate of cysteine of white clover
(*Trifolium repens*) in combination with ammonium nitrate
and triclopyr.

| | lb/A | | % Dead | | | |
|---|---|---|---|---|---|---|
| Triclopyr | Ammonium nitrate | Cysteine | Applied 7/20/94, Evaluated 8/1/94 | Applied 7/20/94, Evaluated 8/3/94 | Applied 7/25/94, Evaluated 8/20/94 | Average |
| 2 | — | 0.05 | 45 | 45 | 35 | 40 |
| 2 | 1 | 1 | 50 | 45 | 40 | 45 |
| 2 | 1 | — | 30 | 30 | 40 | 35 |
| 5 | — | — | 50 | 50 | 35 | 45 |

TABLE 9

Response of three resistant weed species to two rates
of cysteine in combination with ammonium nitrate and triclopyr.

| lb/A | | | % Dead | | |
|---|---|---|---|---|---|
| Triclopyr | Ammonium nitrate | Cysteine | Canada thistle[1] | Common milkweed[2] | Chicory[3] |
| 2 | — | — | 40 | 45 | 60 |
| 2 | 1 | 0.05 | 50 | 60 | 80 |
| 2 | 1 | 1 | 40 | 20 | 80 |
| 1 | — | — | 60 | 50 | 80 |

[1]*Circisum arvense*. Applied 7/26/94. Evaluated 8/20/94.
[2]*Asclepias syriaca*. Applied 7/27/94. Evaluated 8/20/94.
[3]*Chicorium intybus*. Applied 7/28/94. Evaluated 9/12/94.

TABLE 10

Weed control by 2 lb/A triclopyr with or without ammonium nitrate or cysteine on wild carrot (*Daucus carota*),
Canada thistle (*Cirsicum arvense*), whorled milkweed (*Asclepias verticillata*), common milkweed
(*Asclepias syriaca*), field bindweed (*Convolvulus arvensis*), chicory (*Chichorium intybus*), white clover
(*Trifolium repens*), red clover (*Trifolium pratense*) aster (Aster spp.) and goldenrod (Solidago spp.).

| 2 lb/A Triclopyr plus | | | | | | | | % Dead | | | | | | |
|---|---|---|---|---|---|---|---|---|---|---|---|---|---|---|
| Ammonium nitrate | Cysteine | Wild carrot | | Canada thistle | Milkweed whorled | Milkweed common | | Field bindweed | Chicory | | Clover, white | | Clover, Red | Aster/goldenrod | Average all species |
| 0 | 0 | 30[1] | 30[7] | 30[2] | 50[5] | 0[13] | 20[4] | 20[12] | 100[4] | 20[6] | 10[11] | 20[9] | 15[10] | 30[10] 30[12] | 20[15] | 30 |
| 1 | 0 | 30 | 30 | 40 | 80 | 0 | 40 | 20 | 100 | 30 | 10 | 30 | 30 | 40 30 | 20 | 35 |
| 0 | 1 | 35 | 30 | 30 | 70 | 20 | 55 | 30 | 100 | 30 | 20 | 35 | 20 | 40 40 | 20 | 40 |
| 0 | 1 | 40 | 40 | 50 | 65 | 20* | 80 | 100 | 100 | 45 | 25 | 40 | 25 | 50 50 | 25** | 53 |
| 1 5 lb/A triclopyr | — | 40 | 40 | 60 | 80 | 30* | 100 | 100 | 100 | 50 | 30 | 30 | 30 | 50 50 | 30** | 53 |

[1]Applied 7/29/94. Evaluated 8/20/94.
[2]Applied 8/1/94. Evaluated 8/20/94.
[3]Applied 8/3/94. Evaluated 8/20/94.
[4]Applied 8/3/94. Evaluated 9/8/94.
[5]Applied 8/4/94. Evaluated 8/16/94.
[6]Applied 8/6/94. Evaluated 8/20/94.
[7]Applied 8/8/94. Evaluated 8/20/94.
[8]Applied 8/9/94. Evaluated 9/12/94.
[9]Applied 8/10/94. Evaluated 8/20/94.
[10]Applied 8/11/94. Evaluated 9/3/94.
[11]Applied 8/15/94. Evaluated 9/3/94.
[12]Applied 8/17/94. Evaluated 9/3/94.
[13]Applied 8/19/94. Evaluated 9/3/94.
[14]Applied 9/22/94. Evaluated 9/3/94.
[15]Applied 9/24/94. Evaluated 10/9/94.
*100% dead 9/14/94.
**Resistant, not killed.

In addition, a series of date and rate tests were conducted between Aug. 9, 1994 and Aug. 25, 1994. A mixture of 2 lb/A triclopyr, 1 lb/A ammonium nitrate and 0.05 lb/A cysteine was applied at ½×, 1×, 1.5×, 2×, 2.5× and 3× on August 9, August 11, August 16, August 18, August 23 and August 25. Species treated included common milkweed (*Asclepias syriaca*), field bindweed (*Convolvulus arvensis*), ground cherry (*Physalis heterophylla*), dogbane (*Apocynum cannabinum*), wild carrot (*Daucus carota*), red clover (*Trifolium pratense*), whorled milkweed (*Asclepius verticillata*), canada thistle (*Cirsicum arvense*), evening primrose (*Oenothera biennis*), wild lettuce (*Latuca canadensis*), chicory (*Chicorium intybus*), dandelion (*Taraxacum officinale*), buckthorn plantain (*Plantago lanceolata*), common plantain (*Plantago major*), creeping charlie (*Glecoma hederacea*) and poison ivy (*Rhus radicans*). Complete control of all species was attained at the 2× rate of application (4 lb/A triclopyr plus 2 lb/A ammonium nitrate plus 0.1 lb/A cysteine).

It is evident from the above results that the use of thiol compounds in conjunction with auxin like compounds as herbicides greatly enhances the efficiency of cytotoxicity of the herbicide. Substantially lower rates of application can be employed than previously employed to obtain substantially complete eradication of weeds and other undesired vegetation.

II. Use of Thiol Compounds as Root Formation Enhancers

The following study is directed to rooting of microcuttings produced from callus, using auxin shock, followed by treatment with a thiol compound pf malus, Daphne and Dipladnia.

Materials and Methods

Rooting of microcuttings produced from callus of *Malus domestica* Borkh., Dipladenia and *Daphne odorata varigata* was studied. All three species were rooted using the same technique. Shoots (2 cm) were harvested at the end of the multiplication medium and were placed for 1 h (Dipladenia) or 2 h (Malus and Daphne) on a highly concentrated agarised solution of IAA at 1 mM (Dipladenia and Daphne) or 2 mM IAA (Malus). After this auxin treatment, the micro cuttings were transferred to a hormone-free medium, containing the thiol compound, dithiothreitol, at different molarities, to allow root formation to proceed.

The plants were first placed in the dark for 6 days at 26° C. and then transferred to the culture room. The auxin (IAA) was solubilized in 70% alcohol and the pH adjusted to 5.5. The auxin treatment took place in plastic jars and rooting was in glass tubes closed with Magenta caps. The actual multiplication and root expression media varied according to the species involved.

1) Malus: For the trials, we used two apple rootstocks (Jork 9 and Cepiland) which were cultured in vitro. The proliferation phase took place on a Murashige and Skoog (1962) (Need citation) mineral solution with 100 mg/l inositol, 1 mg/l thiamine-HCL, 0.5 mg/l nicotinic acid, 0.5 mg/l pyridoxine-HCl, the plant growth regulators benzyladenine (1 mg/l) and indole-butyric acid (0.1 mg/l), and sucrose (30 g/l) (MSO medium). The pH was adjusted to 5.5. The culture conditions were: temperature 20°–22° C., photoperiod 16 h and light (mol/m2/s). To further propagate the plants, 0.5 cm apical shoots were excised and transferred to a fresh medium. After 6 weeks, tufts of shoots between 1 to 3 cm in length were formed.

2) Daphne: An in vitro culture of *Daphne odorata varigata* was used. The multiplication medium was a Woody Plant Medium (WPMO) mineral solution (Lloyd and McCown 1981) (Need citation) supplemented with vitamins (Mullin et al. 1974) (Need citation) and amino acids (Skoog 1944) (Need citation). The plant growth regulators were benzylaminopurine 0.5 mg/l and α-naphthylacetic acid 0.01 mg/l. Sucrose and Difco bactoagar were added at 20 g/l and 9 g/l respectively, after adjusting the pH to 5.5.

3) Dipladenia: An in vitro culture of Dipladenia was used. The multiplication medium was based on Murashige and Skoog (1962) mineral, vitamin and amino acid solutions supplemented with 4 mg/l 2iP (2-isopentyladenine) and 0.2 mg/l indolebutyric acid. Sucrose and agar (Sigma 9915) at 30 g/l and 7 g/l respectively were added after adjusting the pH to 5.7. The root expression media were identical to the multiplication media but were hormone free (i.e. a MSO medium for Malus and Dipladenia, and a WPMO medium for Daphne).

The auxin shock utilized indole-3-acetic acid (IAA). The short treatment with auxin was a 2 h dip of the base of the cutting (2–3 mm) in an agarised solution of 1 or 2mM IAA. The shoots were then transferred (rinsed) directly to agar medium for rooting.

With Malus, to investigate the timing of dithiothreitol action on rooting, one experiment was with different incubation timings. One application was during the induction phase (during 5 days following the auxin shock), then the cuttings were transferred to MSO medium. Another application was during the expression phase (after 5 days on MSO medium), then the cuttings were transferred to the medium with various DTT concentrations (day 5 to day 21).

In woody plant experiments, each treatment consisted of 22 or 33 cuttings. Experiments were repeated 2 times. Rooting was measured as the number of roots per cutting after 2 and 3 weeks following the auxin shock for *Malus domestica* var Jork 9 (easy to root) and *Malus domestica* var Cepiland (difficult to root) and 3 and 4 weeks following the auxin shock for *Daphne odora* (difficult to root) and 4, 6, and 8 weeks for Dipladenia (difficult to root).

Statistical data are expressed using GBStat software one, two or three way analysis of variance and means comparison by Dunnett Test at 0.05. The test compares the control treatment (DTT=0). Data are presented as the probability level for each treatment and as the results of the Dunnett's Test.

RESULTS

Daphne odora

*Daphne odorata* has always been considered as a difficult-to-root species. In our experiments, rooting was greatly improved by using DTT at low concentration (0.1 to 0.25 mM) (Table 10) after 4 weeks following auxin shock.

Another aspect of using DTT is the absence of callus formation at the base of the microcuttings. Large callus are always developing in multiplication medium of rooting without DTT but not in its presence.

Dipladenia

In these experiments, cuttings were obtained either from apical shoot segments (apex) or from mononodal shoot segments. After 8 weeks, the rooting was highly improved using apex cuttings, and after auxin shock, incorporating DTT in the rooting medium at concentrations of 0.1 or 0.25mM (Table 11). As in the Daphne experiments, we also noticed the absence of callus formation in plants treated with DTT.

*Malus domestica* var Jork 9

With this "easy-to-root" rootstock strain, use of DTT consistently promoted adventitious rooting. Best results were at concentrations of 0.35 and 0.3mM of DTT (Table 12). After 3 weeks, the cuttings without auxin shock did not give a significant number of roots either in the presence of in the absence of DTT.

*Malus domestica* var Cepiland

This strain of Malus rootstock is more difficult to root than Jork 9. At 3 weeks after auxin shock, the application of DTT under the same conditions as Jork 9 always gave results significantly better than the controls without DTT. The absence of an auxin shock did not induce a significant number of roots (Table 13). Higher concentrations of DTT compared with Jork 9 were required to give the best results in the preparation of plants producing roots and in the mean number of roots/plants.

TABLE 11

Rooting of *Daphne odora* after auxin shock in the presence of varying concentrations of DTT. Data are expressed as % of rooting and number of roots and mean comparison by Dunnett Test at 0.05. Means with the same letter are not different from the control (p < 0.001).

| DTT, mM | Rooting, % | Roots/plant |
|---|---|---|
| 0.00 (control) | 18$^a$ | 0.21$^a$ |
| 0.1 | 63 | 2.70 |
| 0.25 | 54 | 1.42 |
| 0.50 | 30$^a$ | 0.64 |

TABLE 12

Rooting in Dipladenia apical cuttings. The best rooting response was with 0.25 and 0.1 mM dithiothreitol (DTT) after 8 weeks. Means with the same letter are not different from the control (p < 0.001).

| Type of cutting | Auxin shock | DTT, mM | Roots/plant | % |
|---|---|---|---|---|
| Apex | − | 0.00 | 1.6$^a$ | 13$^a$ |
|  |  | 0.1 | 1.9$^a$ | 15$^a$ |
|  |  | 0.25 | 2.3$^a$ | 15$^a$ |
|  | + | 0.00 | 3.3$^a$ | 30$^a$ |
|  |  | 0.1 | 4.3$^a$ | 77 |
|  |  | 0.25 | 6.5$^a$ | 89 |
| Node | − | 0.0 | 0.0 | 0 |
|  |  | 0.1 | 0.8 | 9 |
|  |  | 0.25 | 1.1 | 10$^a$ |
|  | + | 0.00 | 0.3 | 2 |
|  |  | 0.1 | 0.3 | 5 |
|  |  | 0.25 | 1.1 | 9 |

TABLE 13

Response of cuttings of *Malus domestica* var Jork 93 weeks after auxin shock. Means with the same letter are not different from the control.

| DTT, mM | Rooting, % | Roots/plant |
|---|---|---|
| 0.0 | 73$^a$ | 3.45$^a$ |
| 0.1 | 77$^a$ | 3.77$^a$ |
| 0.15 | 91 | 3.77$^a$ |
| 0.2 | 82$^a$ | 4.09 |
| 0.25 | 91 | 4.95 |
| 0.3 | 96 | 6.14 |
| 0.5 | 77$^a$ | 3.23$^a$ |
| 1.0 | 73$^a$ | 2.55$^a$ |
| 2.0 | 23 | 0.23 |

TABLE 14

Effect of DTT concentration on rooting of *Malus domestica* var Cepiland cuttings. Means with the same letter are not different from the control (p < 0.05).

| DTT, mM | Rooting, % | Roots/plant |
|---|---|---|
| 0.0 (control) | 77$^a$ | 2.59$^a$ |
| 0.1 | 73$^a$ | 1.82$^a$ |
| 0.25 | 68$^a$ | 1.68$^a$ |
| 1.0 | 91 | 4.64 |

In the next study, species *Glycine max*, *Phaseolus aurus* and *Malus domestica* were studied. In addition, the thiol treatment was varied as to the time administered after the auxin shock.

Rooting of Shoots of Soybean and Mungbean

Seed of soybean (*Glycine max*, var Williams) or mungbean (*Phaseolus aureus*) were soaked in water for several hours, planted in moist vermiculite and germinated and grown in the greenhouse for about 2 weeks. Shortly after the epicotyl was fully extended but before the expansion of the first trifoliate leaf, shoots were harvested by cutting just above the roots and transferred to shell vials (10 ml) containing 5 ml of aqueous rooting solution. Rooting was continued in the light (fluorescent, 200 mol/m$^2$/s, 8 h light period) for 7 to 10 days. All roots were counted on each of 3 to 5 cuttings in 3 replications. Results are means±standard deviations among replicates.

Micropropagation and Rooting of Shoots of Apple in Culture

The plant was an apple rootstock Jork 9 obtained from B. Kunneman (COST, NL-2160 AB LISSE). The plants were already established in vitro before the start of the experiments.

In the proliferation phase, plants were formed in tufts of shoots varying between 1 and 3 cm in length. To multiply the plants, an apex of 0.5 cm was excised and transferred to fresh medium. Apices were cultured in glass jars containing 100 ml of medium and covered with Saran film (PVDC Dow Chemical). The multiplication medium and the culture room conditions were described in Seingre et al. (1991) Acta Hortic. 289: 151–155. The medium contained MS mineral solution (macro and micro elements) with 100 mg/l inositol, 1 mg/l thiamine HCl, 0.5 mg/l nicotinic acid, 0.5 mg/l pyridoxine HCl, the plant growth regulators benzyladenine (1 mg/l) and indolebutyric acid (0.1 mg/l) and sucrose (30 g/l). The pH was 5.5. The culture conditions were: temperature, 20°–22° C., photoperiod, 16 h and light, 15 W/m$^2$.

For the rooting phase, shoots of 2 cm in length were harvested at the end of the proliferation stage and were given a short treatment with auxin before transfer to a rooting medium (medium identical to the multiplication medium without hormones) to initiate rooting. The sulfhydryl compounds were prepared aseptically by filtration and introduced with the concentrated molten agar rooting medium just before solidification. After transfer, the plants were kept in darkness at 26° C. for 6 days and then returned to the culture room. The auxin treatment and the rooting were in glass jars.

Rooting is expressed as the number of shoots per tuft producing>5 roots. Each treatment was 22 tufts and experiments were repeated 3 times. Rooting was measured as the ratio of the number of roots produced/total number of shoots.

Auxin Shock

The auxin shock utilized indole-3-acetic acid (IAA). The short treatment with auxin was a 2 h dip of the base of the cutting (2–3 mm) in an agarised solution of 2 mM IAA. The shoots were then transferred (rinsed) directly either to agar (apple) or distilled water in shell vials (soy- and mungbean) containing the test substances.

RESULTS

In either the presence and in the absence of auxin, the numbers of roots were about doubled by the addition of the thiol compounds GSH or DTT compared to no auxin shock (−auxin) or the auxin shock alone (+auxin). See Table 15. Both mungbean and soybean showed an optimum curve in the presence of auxin at 0.1 mM for glutathione and 1 mM for dithiothreitol. In the absence of auxin, rooting overall was much less and the optimum was less clear. However in the absence of the auxin shock, rooting appeared to be stimulated at approximately the same concentration as in the presence of 2,4-D especially with soybeans. Low concentrations of dithiothreitol (0.1 to 0.05 mM) appears to inhibit rooting of mungbean shoots in the presence of auxin.

The appearance of the roots for soybean shows striking differences. Roots in the presence of glutathione or dithiothreitol were not only more numerous but generally were longer than the roots of comparable control shoots treated either in the absence or presence of the auxin shock. Additionally, with dithiothreitol and glutathione, roots formed higher on the stem.

In addition to improving the quality of roots formed in the presence of the auxin shock, glutathione and dithiothreitol also improved shoot elongation following the auxin shock (Table 16). With auxin shock alone, shoot growth was reduced by approximately 50%. At optimum concentrations of glutathione and dithiothreitol for rooting, shoot growth in the presence of auxin was restored nearly to levels in the absence of auxin.

With Malus cuttings growing in agar, the thiol compounds were not only effective in rooting but also promoted shoot growth. As with soybean and mungbean, the compounds were effective both in the presence and in the absence of an auxin shock. See Table 17.

TABLE 15

Rooting of soybean shoots promoted by glutathione and dithiothreitol in the presence and absence of auxin shock (2 mM IAA, 2h)
Results are means of ten shoots in each of 3 replicate trials ± standard deviations among trials.

| Treatment | Roots per shoot | |
| --- | --- | --- |
|  | −Auxin | +Auxin (2 mM) |
| None | 15 ± 3 | 28 ± 1 |
| Glutathione (0.25 mM) | 22 ± 2 | 45 ± 6 |
| Dithiohreitol (0.5 mM) | 21 ± 4 | 40 ± 5 |

TABLE 16

Shoot length of soybean promoted by glutathione and dithiothreitol in the presence and absence of auxin shock (2 mM IAA, 2h).
Results are means of ten shoots in each of 3 replicate trials ± standard deviations among trials.

| Treatment | Shoot length cm | |
| --- | --- | --- |
|  | −Auxin | +Auxin (2 mM) |
| None | 10 ± 2 | 5 ± 1.5 |
| Glutathione (0.1 mM) | 12 ± 3 | 12 ± 2 |
| Dithiohreitol (1 mM) | 7 ± 1 | 9 ± 1 |

TABLE 17

Rooting of soybean promoted by dithiothreitol and effects on root length. Results are means of three replicates of 10 shoots each ± standard deviation among replicates.

| Treatment | Dithiothreitol | Roots | |
| --- | --- | --- | --- |
|  |  | Number/cutting | Length (cm) |
| Control (water only) | None | 13 ± 1 | 2.5 ± 0.5 |
| Auxin shock | None | 19 ± 3 | 0.45 ± 0.05 |
| Auxin shock | 0.1 mM | 40 ± 10 | 4.1 ± 0.5 |
| Auxin shock | 0.3 mM | 53 ± 13 | 3.0 ± 0.4 |

TABLE 18

Response of rooting of Malus var Jork 9 to glutathione (GSH), 3 weeks after auxin shock. Means followed by the same letter are not different from controls (p > 0.001).

| GSH | Rooting, % | Roots/Plant, number |
| --- | --- | --- |
| 0.0 (Control) | 73[a] | 3.45[a] |
| 0.1 | 77[a] | 3.77[a] |
| 0.15 | 91 | 3.77[a] |
| 0.2 | 82[a] | 4.09 |
| 0.25 | 91 | 4.95 |
| 0.3 | 96 | 6.14 |
| 0.5 | 77[a] | 3.23[a] |
| 1.0 | 73[a] | 2.55[a] |
| 2.0 | 23 | 0.23 |

TABLE 19

Rooting of Hedera cuttings after 1 month promoted by dithiothreitol. Results are mean of replicated determinations of 6 to 9 cuttings/treatment ± mean averages deviations between the means.

| Treatment | Roots/cutting | Cuttings with no Roots, % |
|---|---|---|
| Control (water only) | 2 ± 1 | 33 |
| Auxin shock | 5 ± 2 | 30 |
| Auxin shock + 0.1 mM dithiothreitol | 13 ± 9 | 10 |
| Auxin shock + 0.3 mM dithiothreitol | 13 ± 0 | 0 |

Alternative Rooting Procedure

The initial step can be reached by a one day auxin shock with indolebutyric acid (25 μM) on stem discs or 2 h IAA shock (1 mM) on shoots. Both treatments are enough for induced formation of roots in Malus Jork 9. Root induction is obtained in the 4–5 days following the auxin shock, root elongation of expression needing 3 to 5 days more. The time of DTT application in the subsequent steps give results that show promoting effects of DTT. In one experiment, with application of DTT at the time of induction or at the time of expression, preliminary results showed that action of DTT was similar for the induction phase as well as the expression phase.

In herbaceous plants, easy-to-root, the response to DTT and GSH is nearly double the amount of roots produced both in the presence or absence of auxin treatment. With woody plants, which are more difficult to root than herbaceous, the best response is given with only the DTT in the presence of auxin or in auxin shock.

III. Effect of Thiol Compounds on Cytotoxicity of Anticancer Compounds With Cancer Cells The use of cysteine in combination with an an antitumor sulfonylurea LY181984 (N-(p-tolylsulfonyl),N-(p chlorophenyl) urea. The compositions were tested employing HeLa cells in culture. Mammalian cells were grown in 175 cm² flakes in minimum essential medium at 37° C. with 10% bovine calf serum (heat inactivated). Cell proliferation was determined by direct cell counts using a hemacytometer. Cysteine at a concentration of 100 μM was without effect on growth of HeLa cells, but in the presence of 100 μM LY181984 was effective in preventing HeLa cell growth. Cysteine was effective in enhancing the activity of 100 μM LY181984 over the concentration range of 10 to 1000 μM (all concentrations equally effective) (Table 19). Concentrations lower than 10 μM were not tested.

With longer periods of growth the combination of LY181984 plus cysteine began to result in programmed cell death (apoptosis) of the treated cells (Table 18). Overall, the effect of the cysteine was to increase the effectiveness of LY181984 by approximately two log orders, i.e. approximately 100 times less LY181984 was required to kill the cells in the presence of 100 μM cysteine, than in its absence.

TABLE 20

Response of HeLa cells to LY181984 and effect of varying concentrations of L-cysteine.

| LY181984 | L-cysteine | cells/mm² |
|---|---|---|
| None | None | 933 |
| 100 μM | None | 408 |
|  | 10 μM | 248 |
|  | 100 μM | 268 |
|  | 1000 μM | 242 |

TABLE 21

Cell number after 168 of HeLa cells treated with 100 μM LY181894 in the presence or absence of 100 μM L-cysteine.

| LY181984 | L-cysteine | cells/mm²* |
|---|---|---|
| None | None | 1987 ± 21 |
|  | 100 μM | 2066 ± 36 |
| 100 μM | 100 μM | 395 ± 57 |

*Initial cell number 150 cells/mm² between 72 and 168 h. The number of control cells increased 3.3-fold whereas those treated with cysteine plus LY181984 decreased by 10%. Remaining cells were largely apoptotic.

It is evident from the above results, that the addition of thiol compounds in conjunction with a variety of cell modulating agents can greatly enhance the effectiveness of the cell modulating agent. Thus, with compounds which encourage cell proliferation such as auxins, where the auxin can serve as a herbicide or rooting formulation, thiol compounds are found to enhance the effectiveness of the auxin for its cell modulating effect. With chemotherapeutic agents, particularly those associated with inhibition of a surface membrane NADH oxidase, the thiol compounds substantially enhance the cytotoxic effect, permitting substantially lower concentrations of the cytotoxic agent, while retaining the desired cytotoxic effect.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a method for inhibiting cellular growth of undesired cells using a cytotoxic agent, by contacting said cells with said cytotoxic agent under cytotoxic conditions, the improvement which comprises:

contacting said cells in conjunction with said cytotoxic agent, with a thiol compound in an amount sufficient to enhance the cytotoxic effect of said cytotoxic agent, where said cytotoxic agent is administered in an amount less than the amount required to obtain cytotoxicity in the absence of said thiol compound, wherein said cells are plant cells as part of a growing plant and said cytotoxic agent is an auxin herbicide.

2. A method according to claim 1, wherein said contacting is in conjunction with ammonium nitrate as an adjuvant in an amount sufficient to enhance cytotoxicity.

3. A method according to claim 1, wherein said thiol compound is cysteine, dithiothreitol or glutathione.

4. A method according to claim 1, wherein said herbicide and thiol compound are administered as a spray.

5. The method according to claim 1, wherein said thiol compound has from 2 to 10 carbon atoms.

6. In a method for inhibiting the growth of plants using an auxin herbicide, by contacting said plants with said herbicide under herbicidal conditions, the improvement which comprises:

contacting said plants in conjunction with said herbicide, with a thiol compound in an amount sufficient to enhance the herbicidal effect of said herbicide, where said herbicide is administered in an amount less than the amount required to obtain the same level of plant death in the absence of said thiol compound.

7. A method according to claim 6, wherein said herbicide is 2,4-dichlorophenoxyacetic acid or triclopyr, and is administered at a rate of about 1 to 6 pounds per acre, and said thiol compound is administered at a rate of about 0.01 to 2 pounds per acre.

8. A method according to claim 7, wherein said contacting comprises contacting with from about 0.025 to 2 pounds per acre.

9. The method according to claim 6, wherein said thiol compound has from 2 to 10 carbon atoms.

* * * * *

UNITED STATES PATENT AND TRADEMARK OFFICE
CERTIFICATE OF CORRECTION

PATENT NO.  : 5,643,853

DATED       : July 1, 1997

INVENTOR(S) : Morré

It is certified that error appears in the above-identified patent and that said Letters Patent is hereby corrected as shown below:

Column 6, Line 2, please delete "1-2 mMindole-3-acetic acid" and replace with --1-2 mM indole-3-acetic acid--.

Column 9, Table 4, the last line of the title, please delete "7/20/94, and" and replace with --7/20/94,*** and--.

Column 11, Table 10, Footnote 14, please delete "9/22/94" and replace with --8/22/94--.

Column 11, Table 10, Footnote 15, please delete "9/24/94" and replace with --8/24/94--.

Column 14, Line 54, please delete "*Daphne odora*" and replace with --*Daphne odorata*--.

Column 15, Line 17 - 18, please add --or-- between "presence of" and "in the absence".

Column 16, Table 13, the first and second line of the title, please delete "var Jork 93 weeks" and replace with --var Jork 9, 3 weeks--.

Signed and Sealed this

Twenty-third Day of December, 1997

Attest:

Attesting Officer

BRUCE LEHMAN

Commissioner of Patents and Trademarks